United States Patent [19]

Creuzet et al.

[11] Patent Number: 4,698,343
[45] Date of Patent: Oct. 6, 1987

[54] (ALKOXY-2)PHENYLPIPERAZINES HAVING ALPHA-1 AND BETA BLOCKING PROPERTIES

[75] Inventors: Marie-Helene Creuzet, Bordeaux; Claude Feniou, Pessac; Francoise Guichard, Rue St Elisabeth; Henri Pontagnier, Pessac; Gisele Prat, Talence, all of France

[73] Assignee: Societe Cortial, S.A., Paris, France

[21] Appl. No.: 777,530

[22] Filed: Sep. 19, 1985

[30] Foreign Application Priority Data

Sep. 19, 1984 [FR] France ................ 84 14579
Jul. 26, 1985 [FR] France ................ 85 11574

[51] Int. Cl.[4] .............. A61K 31/495; C07D 241/04
[52] U.S. Cl. ........................... 514/255; 544/392; 544/394
[58] Field of Search ............. 544/394, 392; 514/255

[56] References Cited

U.S. PATENT DOCUMENTS 3,951,983  4/1976  Danilewicz et al. ............ 544/394
3,951,986  4/1976  Maruyama et al. ............. 544/394
4,012,444  3/1977  Lunts et al. .................... 564/164
4,202,978  5/1980  Fahrenholtz et al. ........... 544/394

FOREIGN PATENT DOCUMENTS 743494  12/1969  Belgium ........................... 544/394
0005142  8/1978  European Pat. Off.
2416888  2/1979  France.
1317479  5/1973  United Kingdom ............ 544/394

OTHER PUBLICATIONS

Lunts, Chem. Abst: 75-5520c (1971).

Primary Examiner—Donald G. Daus
Assistant Examiner—Cecilia Shen
Attorney, Agent, or Firm—Oblon, Fisher, Spivak, McClelland, & Maier

[57] ABSTRACT

A compound of the formula

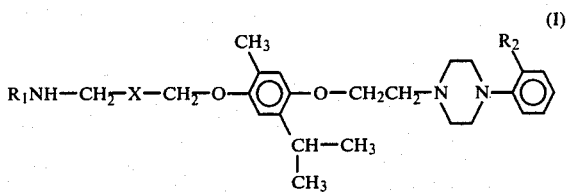

wherein $R_1$ is $C_3$-$C_6$ branched alkyl group, e.g., an isopropyl group or a tert-butyl group, $R_2$ is a $C_1$-$C_6$ alkoxy group, e.g., a methoxy, an ethoxy or a propoxy group, and X is a CHOH group or a $(CH_2)_n$—group where n=0, 1 or 2 and a process for making this compound are disclosed.

This compound is useful in human and veterinary therapeutics.

14 Claims, No Drawings

(ALKOXY-2)PHENYLPIPERAZINES HAVING ALPHA-1 AND BETA BLOCKING PROPERTIES

BACKGROUND OF THE INVENTION

1. Field of the Invention

This invention relates to (alkoxy-2)-phenylpiperazine derivatives, methods for their preparation and their therapeutic application.

2. Discussion of the Background

Compounds which combine alpha and beta blocking properties are known. Thus, labetalol (U.S. Pat. No. 4,012,444) is utilized therapeutically in the treatment of hypertension. French patent No. 7902733, filed by the Hoffman-la-Roche Company on Feb. 2, 1979 discloses derivatives of phenyl piperazine, of the formula (II)

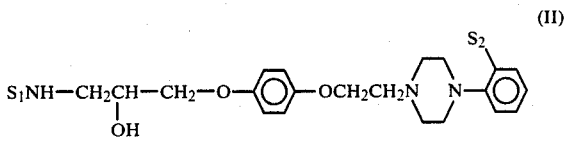

where $S_1$ is a lower alkyl group and $S_2$ is a hydrogen atom or a lower alkoxy group.

SUMMARY OF THE INVENTION

It is an object of this invention to provide novel compounds capable of blocking alpha-1 and beta-adrenergic receivers.

It is another object of this invention to provide a novel compound having very long duration anti-hypertensive properties.

It is another object of this invention to provide a novel compound having excellent alpha-1 and beta blocking properties at very low doses of administration.

It has now suprisingly been discovered that all of these objects are fully satisfied with the compound of the formula (I)

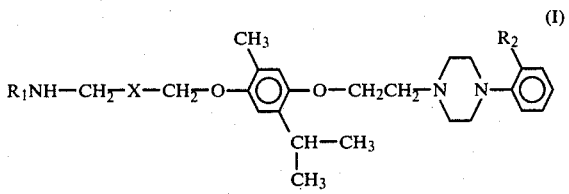

wherein:
- $R_1$ is a $C_3$–$C_6$ branched alkyl group such as, e.g., isopropropyl or tert-butyl;
- $R_2$ is a $C_1$–$C_6$ alkoxy group, such as, e.g., a methoxy, an ethoxy, or a propoxy group; and
- X is a CHOH group or a $(CH_2)_n$ group, where n=0, 1 or These compounds can be in any pharmaceutically acceptable free base form or acid salt form. For example, they can be in their chlorhydrate form.

DISCUSSION OF THE PREFERRED EMBODIMENTS

The compounds of formula (I) have very long duration anti-hypertensive properties related to their blocking of alpha-1 and beta-adrenergic receivers.

The present compounds, when X is a —CHOH— group, differ from the compounds described in French patent No. 7902733 by having a methyl and an isopropyl substituant on the paraphenylenedioxy nucleus. This substitution unexpectedly gives rise to excellent alpha-1 and beta blocking properties with very small doses of administration.

The present compounds maybe prepared by the reaction of a ((halogeno-ethoxy)-4-isopropyl-5 methyl-2-phenoxy)alkylamine of formula (III)

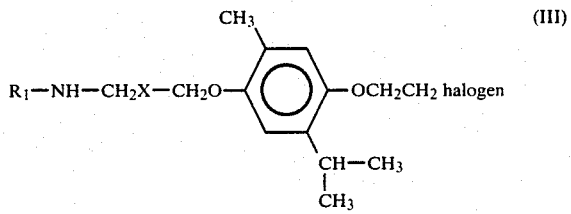

wherein $R_1$ is a $C_3$–$C_6$ branched alkyl group, e.g., an isopropyl group or a tert-butyl group, X is a CHOH group or a $(CH_2)_n$ group, with n=0, 1 or 2, and halogen is a chlorine or a bromine atom, with an (alkoxy-2-phenyl)piperazine of formula (IV)

wherein $R_2$ is a $C_1$–$C_6$ alkoxy group, e.g., a methoxy, an ethoxy, or a propoxy group, in the presence of a base, such as an amine, in a solvent. Any amine may be used, with tripropyl amine and especially triethylamine being preferred. Likewise, any solvent capable of solvating the reagents may be used, with alcoholic solvents and especially ethanol being preferred.

The present compounds can also be prepared from a ((alkoxy-2 phenyl)piperazinyl-2-ethoxy)-4-isopropyl-5-methyl-2-phenol of the formula (V)

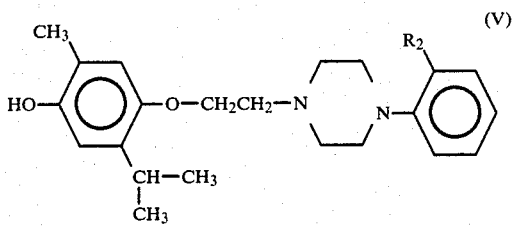

wherein $R_2$ is a $C_1$–$C_6$ alkoxy group, preferably a methoxy, an ethoxy, or a propoxy group.

When X is a $(CH_2)_n$ group, where n=0, 1 or 2, a phenol of formula (V) is made to react with a dibromolkane of formula (VI)

Br-$CH_2$-X-$CH_2$-Br (VI)

The bromine derivative thus obtained is then made to react with an alkylamine of formula (VII)

$R_1NH_2$ (VII)

wherein $R_1$ is a $C_3$–$C_6$ branched alkyl group, such as, e.g., an isopropyl group or a tert-butyl group.

When X is a CHOH group, one can prepare, from the phenol of formula (V), an epoxy compound of the formula (VIII)

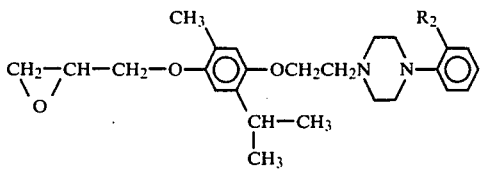

This epoxy compound reacts with the alkylamine of formula (VII) to give the compound of formula (I) where X=CHOH. The epoxy compound (VIII) can be obtained via several methods. One can, for example, react the phenol compound of formula (V) with an allyl bromide in the presence of acetone and potassium carbonate to obtain the corresponding allyl ether. This allyl ether is then converted to the corresponding epoxy compound by reaction with N-bromoacetimide and perchloric acid. In a variation of this method, the phenol of formula (V) is rated with the epichlorohydrin

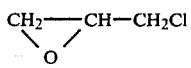

to obtain the epoxy compound (VIII).

Other features of the invention will become apparent in the course of the following description of exemplary embodiments which are given for illustration of the invention and are not intended to be limiting thereof.

EXAMPLE 1

Preparation of the dichlorhydrate of (isopropyl-5 (((methoxy-2-phenyl)piperazinyl)-2 ethoxy)-4-methyl-2-phenoxyl)-1-isopropyl-amino-3-propanol-2; compound of formula I with $R_1$=isopropyl, $R_2$=methoxy, X=CHOH, in dichlorhydrate form. Code name COR28 48.

Synthesis

A mixture of 2.7 g of (bromo-2 ethoxy)-4 isopropyl-5 methyl-2 phenol, 20 ml of acetone, 2.5 ml of allyl bromide and 2.2 g of potassium carbonate is heated under reflux for 11 hours. The solvent is evaporated under the vacuum of a water aspirator. The residue is then taken up in 100 ml of water.

The aqueous phase obtained is extracted twice with 50 ml of ethyl ether. The organic phases are combined, washed with 1N soda, washed with water up to neutrality, dried over sodium sulphate, and then distilled.

An allyl ether of (bromo 2 ethoxy)-4-isopropyl-5-methyl-2-phenol residue which is sufficiently pure to be utilized for the remainder of the synthesis is obtained in a 96% yield.

7.5 g of N-bromoacetamide are added in 12 mn to a mixture of 11.2 g of the allyl ether, 180 ml of acetone and 0.36 ml of 70% perchloric acid.

This reaction mixture is stirred at room temperature for 2.5 hours, the perchloric acid is neutralized with sodium bisulphite, and the solvent is removed by distillation under a vaccum.

The residue obtained is taken up in 100 ml of water and the aqueous phase is extracted twice with 50 ml of ethyl ether.

The ether phases are combined, dried over sodium sulphate, then distilled. The oily residue is dissolved in 250 ml of methanol to which 73 ml of 1N soda are added. This solution is stirred at room temperature for 2 hours, and the methanol then distilled.

The new distillation residue is dissolved in 200 ml of water. The aqueous phase is extracted twice with 50 ml of ethyl ether. The organic phases are combined, washed with water, dried, then distilled. The residual product which consists of the desired epoxy compound is purified by chromatography in an open silica column by successive elutions with pure toluene, then with a gradient of ethyl acetate in toluene.

The overall yield of this stage is 46% based on the allyl ether used.

A mixture of 6.7 g of the epoxy compound, 1.8 g of isopropylamine and 50 ml of methanol is stirred under argon for 3 hours at 60 degrees C.

After distillation under vacuum, the residue is taken up in dilute chlorhydric acid. The new phase is extracted successively with 2×100 ml of ethyl ether, and then 2×100 ml of chloroform. The ether phases are set aside. The chloroform phases are collected, dried, and concentrated. At this time, hot ethyl ether is added to the reaction medium until it becomes slightly cloudy. The reaction medium is then cooled to 5 degrees C.

A white precipitate formed is filtered, dissolved in 50 ml of water, and then next alkalinized by adding 1N soda. This aqueous solution is extracted with 2×30 ml of ethyl ether. The ether phases are collected, washed with water until neutral, dried, then distilled. ((Bromo-2 ethoxy)-4-isopropyl-5-methyl-2-phenoxy)-1-isopropylamino-3-propanol-2 is obtained in a 47% yield.

A mixture of 3.88 g of ((bromoethoxy)-4-isopropyl-5-methyl-2-phenoxy)-1-isopropylamino-3 propanol-2, 1.92 g of (methoxy-2 phenyl)piperazine, 10 ml of triethylamine and 20 ml of ethanol is maintained at reflux for 4 hours. The reaction is followed by thin layer chromatography on silica plates (eluant: $CHCl_3$=80/$CH_3OH$=20/Peak B7) and in high performance liquid chromatography on a G8 column (eluant: $CH_3OH$=70/$H_2O$=30, V/V, flow=1.5 ml/mn).

The mixture is cooled to room temperature, then alkalinized. The solvent is distilled, and the residue taken up in 100 ml of chloroform. The chloroform phase is washed with water until neutral, dried and concentrated. The addition of ethyl ether and cooling of the reaction medium to 5 degrees C cause the formation of a precipitate which is filtered, washed with ethyl ether and dried.

(Isopropyl-5-(((methoxy-2 phenyl)piperazinyl)-2-ethoxy)-4-methyl-2-phenoxy)-1-isopropylamino-3-propanol-2 is obtained in a 52% yield relative to the bromine derivative. This product is transformed into its dichlorhydrate by passing a flow of gaseous HCL over the methanol solution.

Physicochemical properties

Melting point of the dichlorhydrate measured on Mettler apparatus:

88 degrees C.

NMR spectrum of the dichlorhydrate in the DMSO($d_6$): 1.2 and 1.3 ppm(12 protons, doublets, 2 (C(CH$_3$)$_2$)); 2.2 ppm( 3 protons, singlet, phenylic CH$_3$); 2.7–4.7 ppm( 22 protons, complex mass, 8 CH$_2$+3 CH+OCH$_3$ at 3.8 ppm); 6.5 ppm( 1 proton, wide peak, OH, exchangable with D$_2$O); 6.7–7.2 ppm( 6 protons, complex mass, aromatic protons); 9.2 ppm( 2 protons, dome, +NH$_2$, exchangable with D$_2$O); 12 ppm( 1 proton, dome, +NH, exchangable with D$_2$O).

EXAMPLE 2

Dichlorhydrate of ((((ethoxy-2 phenyl) piperazinyl)-2-ethoxy)-4-isopropyl-5-methyl-2-phenoxy)-1 isopropylamino-3-propanol-2 or COR 28 75; dichlorhydrate of the compound of formula (I) in which R1=isopropyl, R2=ethoxy, X=CHOH.

Synthesis

A mixture of 16 g of ((bromo-2 ethoxy)-4-isopropyl-5-methyl-2-phenoxy)-1-isopropylamino-3-propanol-2 prepared according to example 1, 8.5 g of (ethoxy-2-phenyl)piperazine, 100 cm³ of ethanol and 5 cm³ of triethylamine is heated for 6 hours under reflux. The solvent is evaporated. The residue is dissolved in dilute chlorhydric acid (1N), then extracted twice with ether and twice with chloroform. The chloroform is evaporated; the chlorhydrate is neutralized and the base is purified on a silica column by elution with a chloroform (90)—methanol (10) mixture. One thus obtains 4 g of ((((ethoxy-2-phenyl)-piperazinyl)-2-ethoxy)-4-isopropyl-5 methyl-2-phenoxy)-1-isopropylamino-3-propanol-2 in a yield of, 19%. The chlorhydrate is prepared by dissolving the base in ether and by passing a gaseous chlorhydric acid current until the precipitation is complete. It is next filtered and washed with ether.

Physicochemical propertie

Hygroscopic product

NMR spectrum of the dichlorhydrate in the DMSO($d_6$): 1.0–1.7 ppm( 15 protons, complex mass, 2 $C(CH_3)_2$+$CH_3$ of the ethoxy-2 phenyl group); 2.2 ppm( 3 protons, singlet, $CH_3$ in the thymyl ring; 2.9 4.8 ppm 21 protons, complex mass, 9 $CH_2$+—3CH—); 6.7–7.2 ppm 6 protons, complex mass, aromatic protons); 9.3 ppm, (2 protons, dome, +$NH_2$, exchangable with $D_2O$); 12.2 ppm, (1 proton, dome, +NH, exchangable with $D_2O$).

EXAMPLE 3

Dichlorhydrate of N-isopropyl N-(((((methoxy-2 phenyl)piperazinyl)-2 ethoxy)-4 isopropyl-5 methyl-2 phenoxy)-3 propyl)amino or COR28 79; dichlorhydrate of the product of formula (I) with $R_1$=isopropyl, $R_2$=methoxy, X=$CH_2$.

Synthesis

In a three-necked flask, 12 g of ((methoxy-2-phenyl)-piperazinyl)-2-ethoxy)-4-isopropyl-5-methyl-2-phenol and 31 g of dibromo-1,3-propane are added and heated to 140 degrees C. A solution of 2.5 g of potassium in 26 cm³ of methanol is then added in a dropwise manner. The reaction is relatively vigorous. The reaction mixture is kept stirred for 1 hour at reflux, then filtered hot. The precipitate is rinsed with 10 cm³ of methanol, then with 5 cm³ of dibromo-1,3-propane. The filtrate is brought to reflux under agitation for 10 hours. After cooling, 50 ml of chloroform and 50 ml of water are added. The chloroform phase is decanted and washed several times with 30 ml of 5% iced soda. The chloroform phase is next washed with water, dried and the chloroform is evaporated. The excess dibromopropane is distilled with a vane pump. The raw product is purified on a silica column with chloroform as an eluant. Yield: 30%.

In a reactor, one mixes 6 g of the bromopropoxy derivative thus prepared, 30 cm³ of ethanol, 20 cm³ of isopropylamine and 6 cm³ of triethylamine. The mixture is brought to reflux under agitation for 10 h, then left to cool. The alcohol is evaporated, the residue is taken up in ether and extracted with an aqueous solution of chlorhydric acid. The acid phase is extracted with chloroform. The chloroform phase is dried, concentrated, then ether is added to it. The chlorhydrate precipitates. It is filtered, rinsed with ether and dried. Yield 60%.

Physicochemical properties

Melting point of dichlorhydrate measured on a Mettler FP5 apparatus: 107.8–108.2 degrees C.

NMR spectrum of the dichlorhydrate in the DMSOD6: 1.2 ppm( 6 protons, doublet, $C(CH_3)_2$ on an aromatic cycle); 1.3 ppm( 6 protons, doublet, $NC(CH_3)_2$) ; 1.8–2.5 ppm( 5 protons, complex mass, $CH_3$ on a phenyl cycle and $CCH_2C$); 2.8–4.7 ppm( 21 protons, complex mass, 6 $CH_2$-N+2-CH-+2 $OCH_2$+$OCH_3$ at 3.9 ppm); 6.8–7.3 ppm( 6 protons, complex mass, aromatic protons); 9.1 ppm( 2 protons, domes, NH+ and +$NH_2$, exchangable with $D_2O$).

EXAMPLE 4

Variation for synthesis of the product of example 2 or COR 2875.

Synthesis

To a solution of 210 ml of anhydrous dimethylforamide containing 32 g of (((ethoxy-2-phenyl)-piperazinyl)-2-ethoxy)-4-isopropyl-5 methyl-2-phenol, 298.5 g of NaH is added little by little at room temperature. The reaction mixture is then stirred for about 15 minutes at room temperature. 21 ml of epichlorohydrin is then added, and the reaction mixture is heated for 1 hour at 80 degrees C. The solvent is evaporated with the vane pump. The residue is dissolved in 650 ml of ether, then washed with water. The ether phases are dried. The solvent is evaporated. One thus obtains the epoxy compound in a yield of 96%.

A mixture of 35 g of epoxy compound thus prepared, 41 ml of isopropylamine and 200 ml of methanol is heated on reflux under stirring for one hour. The solvent is evaporated. 800 ml of water and concentrated chlorhydric acid are added up to acid pH. The mixtures extracted, two to three times with 100 ml of chloroform. The aqueous phase is neutralized with ammonia solution, and extracted two more times with chloroform. The chloroform phases are collected, dried, evaporated. The residue is dissolved in 400 ml of methanol. A gaseous chlorhydric acid solution current is passed through the solution. This is concentrated on a Rotavapor. Ether is added. The precipitate is filtered and dried. COR 2875 is thus obtained with a yield of 90% in the form of a hygroscopic powder.

The toxicopharmacological properties of the products which are the subject of this invention are described below.

Toxicity: Administered to mice orally at a dose of 100 mg/kg, COR 2848 does not cause death. It causes 100% mortality when it is administered at 300 mg/kg. Its DL50 is equal to 216 (185–253) mg/kg. The DL50's of COR 2875 and COR 2879 are respectively equal to 563.2 (486–652) and 89.97 (72.90–111.03) mg/kg for oral administration.

Administered to mice intraperitoneally, COR 2848 utilized in a dose of 50 mg/kg causes no mortality. It causes 100% mortality at 100 mg/kg.

Intravenously in mice, the DL50 of COR28 48, COR28 75 and COR 28 79 are respectively equal to 20 (19-21), 26.7 (24-30) and 7.84 (7.11-8.66) mg/kg.

Alpha-1 blocking activity: In vivo, the alpha blocking activity is assessed by determining the antagonism of the hypertension induced by the phenylephrine. The product to be tested is administered intravenously to amylated and bivogotomized rats according to the J. S. Gillespie and T. S. Muir technique (*Br. J. Pharmac. Chemother.*, 1967, 30, 78-87). Indicated below is the maximum activity and the time after which the residual activity is equal to 50% of the maximum activity: $3.1 \times 10^{-7}$ M/kg, $-76.1\%$, 20 mn; $10^{-6}$ M/kg, $-92.7\%$, 45 mn; $3 \times 10^{-6}$ M/kg, $-112.5\%$ 110 mn. The DE50 determined under these conditions for the COR2848 is $4.71 \times 10^{-8}$ mole/kg after 2 mn, $7.55.10^{-7}$ mole/kg after 30 mn and $1.57.10^{-6}$ mole/kg after 60 mn.

Beta blocking activity: administered orally in a dose of 25 mg/kg, COR2848 causes, 30 minutes after it is administered, 83% inhibition of the tachycardia induced in mice by isoproterenol.

Anti-hypertensive activity: the product to be tested is administered orally to spontaneously hypertensile rats. Arterial pressure is measured indirectly by utilizing a sphygmomanometer. For COR 2848 administered in a dose of 50 mg/kg/day for 2 days, the maximum pressure drop observed is respectively 38.5% and 36.7%, the first and the second day of treatment, 6 hours after ingestion. The pressure decreased significantly with respect to the control group during the two days of treatment and post-treatment recuperation.

For COR28 79 administered in a dose of 100 mg/kg/day for 2 days, the maximum pressure drop observed is respectively 31 and 34% for the first and second days of treatment, 1 hour after ingestion. Pressure decreased significantly with respect to the control group during the two days of treatment; this decrease was 31% and 24% respectively, 24 h after the first and second ingestion. Pressure decrease varied between 11 and 22% during the two days of post-treatment recuperation.

Spasmolytic activity: in vitro, COR2848 inhibits, at the concentration of 2 microg/ml, the contractions of a guinea pig ileum by transmural electrical stimulation in an oxygenated Krebs solution.

Anti-cholinergic activity: in vitro, COR2848 utilized in the concentration of 10 microg/ml inhibits the contractions of isolated segments of guinea pig ilea induced by 0.1 microg/ml of acetylcholine.

Taking into account their pharmacotoxicological activities, the products which are the subject of this invention are useful, alone, or combined with other active principles, for example, in the treatment of arterial hypertension, cardiac arrhythmia or in the treatment of glaucoma.

The doses and therapeutic schemas will depend on the subject and the issue to be treated. The products may be administered orally (for example in the form of capsules, tablets, ingestable drops), by injection (solution for intramuscular or intravenous injection), rectally (suppositories), locally (eye washes, ointments, gels). According to the directions, the daily dose will vary from 1 to 100 mg in 1 to 3 doses rectally; the dose administered intravenously may vary between 0.1 and 10 mg. The eye washes will contain 0.05 to 0.5% of the active principle and the ointments or gels will contain 0.5% to 5% of active principle.

Obviously, numerous modifications and variations of the present invention are possible in light of the above teachings. It is therefore, to be understood that within the scope of the appended claims, the invention may be practiced otherwise than as specifically described herein.

What is claimed as new and is intended to be secured by letters patents is:

1. A product of the formula

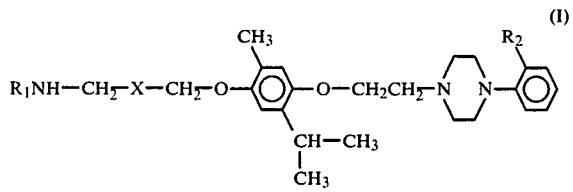

wherein:

$R_1$ is $C_3$-$C_6$ branched alkyl group;

$R_2$ is a $C_1$-$C_6$ alkoxy group; and

X is a CHOH group or a $(CH_2)_n$ group, where n =0, 1 or 2, the said product being in pharmaceutically acceptable free base form or acid salt form.

2. The product of claim 1, wherein $R_1$ is an isopropyl group or a tert-butyl group.

3. The product of claim 1, wherein $R_2$ is a methoxy group, an ethoxy group or a propoxy group.

4. The product of claim 1, wherein the said product is a in chlorhydrate salt form.

5. The product of claim 1, wherein $R_1$ is an isopropyl group, $R_2$ is a methoxy group and X is a $CH_2OH$ group.

6. The product of claim 1, wherein $R_1$ is an isopropyl group, $R_2$ is an ethoxy group and X is a $CH_2OH$ group.

7. The product of claim 1, wherein $R_1$ is an isopropyl group, $R_2$ is a methoxy group and X is a $CH_2$ group.

8. An antihypextensive composition useful in human or veterinary therapeutics comprising a therapeutically effective amount of the compound of claim 1 and a pharmaceutically acceptable vehicle.

9. The composition of claim 8, said composition being in capsule, tablet, ingestable drop, intramuscular injection solution, intravenous injection solution, suppository, eye wash, ointment or gel form.

10. The composition of claim 9, wherein the said composition is an eye wash containing 0.05 to 0.5% of the said compound.

11. The composition of claim 9, wherein the said composition is an ointment or a gel, each containing 0.5 to 5% of the said compound.

12. A method for treating arterial hypertension, cardiac arrhythmia or glaucoma comprising administering to a patient suffering therefrom an effective amount of the compound of claim 1.

13. The method of claim 12, wherein the said administration comprises 1 mg to 100 mg of the said compound administered in 1 to 3 doses rectally.

14. The method of claim 12, wherein the said administration comprises 0.1 mg to 10 mg of the said compound administered intravenously.

* * * * *